US005591144A

United States Patent [19]
Smith et al.

[11] Patent Number: 5,591,144
[45] Date of Patent: Jan. 7, 1997

[54] DRAINAGE BAG

[75] Inventors: Rory J. M. Smith, Hebden; Gillian R. Little, Billericay; Nicholas S. Shelley, Burgess Hill, all of England

[73] Assignee: Welland Medical Limited, Crawley, England

[21] Appl. No.: 448,367

[22] PCT Filed: Nov. 29, 1993

[86] PCT No.: PCT/GB93/02452

§ 371 Date: Aug. 17, 1995

§ 102(e) Date: Aug. 17, 1995

[87] PCT Pub. No.: WO94/12128

PCT Pub. Date: Jun. 9, 1994

[30] Foreign Application Priority Data

Dec. 1, 1992 [GB] United Kingdom ............... 9225071

[51] Int. Cl.⁶ ..................... A61M 1/00; A61F 5/44
[52] U.S. Cl. ............ 604/327; 604/355; 604/332; 604/344; 604/342; 604/346
[58] Field of Search ............ 604/327, 332–344, 604/346, 352, 355; 128/DIG. 24

[56] References Cited

U.S. PATENT DOCUMENTS

| 4,816,027 | 3/1989 | Gilchrist et al. |
| 5,209,744 | 5/1993 | Abe et al. |

FOREIGN PATENT DOCUMENTS

| 0259184 | 3/1988 | European Pat. Off. |
| 0272816 | 6/1988 | European Pat. Off. |
| 0273611 | 7/1988 | European Pat. Off. |
| 0320895 | 6/1989 | European Pat. Off. |
| 0388924 | 9/1990 | European Pat. Off. |
| 1947368 | 8/1975 | Germany. |
| 2064333 | 6/1981 | United Kingdom. |
| 2083762 | 3/1982 | United Kingdom. |
| 2195919 | 8/1986 | United Kingdom. |
| 2185404 | 7/1987 | United Kingdom. |
| 2193925 | 2/1988 | United Kingdom. |
| 2201372 | 9/1988 | United Kingdom. |
| 2227668 | 8/1990 | United Kingdom. |
| 2227937 | 8/1990 | United Kingdom. |

OTHER PUBLICATIONS

International Search Report.
United Kingdom Search Report.

*Primary Examiner*—Robert A. H. Clarke
*Attorney, Agent, or Firm*—Lahive & Cockfield; Anthony A. Laurentano, Esq.

[57] ABSTRACT

The invention provides a drainage bag (e.g. an ostomy bag or the like) for receiving bodily waste, the drainage bag comprising a water-impermeable outer bag; a water-impermeable inner bag enclosed therein; and an orifice to enable bodily waste to be received by the inner bag; the outer and inner bags being detachably secured together in the region of the orifice. The outer and inner bags are preferably detachably secured together by means of frangible or peelable connection or linkage therebetween.

18 Claims, 5 Drawing Sheets

DRAINAGE BAG

BACKGROUND OF THE INVENTION

This invention relates to ostomy bags and like drainage bags, and in particular to bags for which the contents can be disposed of more readily and hygienically by flushing down a W.C.

Ostomy bags for receiving bodily waste from colostomy or ileostomy patients are well known and a major problem with such bags is that it can be difficult to dispose of the used bag in a convenient and hygienic manner.

Often, the contents of used bags are removed by cutting an edge of the bag and depositing the contents into a W.C. for flushing away, leaving the soiled bag for separate disposal, e.g. by incineration or by wrapping and placing in a waste bin. Disposal of a used bag and its contents in this way is clearly unhygienic and unpleasant for the user and, in recognition of this problem, various proposals have been made for ostomy bags which can be flushed down a W.C.:- see for example GB-A-2083762, EP-A-0388924, GB-A-2227668, and GB-A-2193925.

However the ostomy bags currently available suffer from certain drawbacks. Firstly, due to the buoyancy and relative bulk of the bags, it is often difficult to flush them down the W.C. Secondly, in order to ensure that the bag is sufficiently strong and waterproof to withstand the rigours of use, materials have been used which do not decompose readily, if at all, in the sewerage system, thereby giving rise to a pollution problem.

SUMMARY OF THE INVENTION

The present invention seeks to overcome such problems by providing a relatively tough, waterproof detachable outer bag and a water-impermeable inner bag or liner, the inner bag serving to accommodate the bodily waste whilst the outer bag serves as a protective layer. The inner bag is made sufficiently water-impermeable to prevent leakage into the outer bag during the period of use but, because of the existence of the outer bag, need not be made of such durable material. Thus it can be made of material which although water-impermeable over a short period, nonetheless gradually dissolves over a more extended period. The inner bag can therefore be made entirely biodegradable and is ideally suited for disposal by flushing down a W.C. The outer bag which is secured to the inner bag by means of a frangible or peelable connection is torn away from the inner bag after use and, since it is not soiled by the bodily waste can be disposed of with other household refuse.

Accordingly, in a first aspect, the present invention provides a drainage bag (e.g. an ostomy bag or the like) for receiving bodily waste, the drainage bag comprising a water-impermeable outer bag; a water-impermeable inner bag enclosed therein; and means defining an orifice to enable bodily waste to be received by the inner bag; the outer and inner bags being detachably secured together in the region of the orifice.

The outer and inner bags are preferably detachably secured together by means of a frangible or peelable connection or linkage therebetween.

The means defining the orifice can take the form of a flange, for example an adhesive flange of the type conventionally used with ostomy bags. Typically, one surface of the flange is provided with a layer of bioadhesive, e.g. a hydrocolloid adhesive, whilst the inner and outer bags are attached to the other surface of the flange. The inner and outer bags can conveniently be attached to the flange by means of welding, for example thermal welding, or by the use of adhesive or adhesive layers or by a combination of welding and adhesive techniques.

The outer bag preferably is attached by means of a frangible connection to the flange so as to be detachable therefrom, e.g. by tearing along a line of weakness. The line of weakness preferably is in the region of the weld and most preferably is created (e.g. by over-embossing with the welding tool) whilst the outer bag is being welded to the flange.

Alternatively, a peelable union can be provided through the selection of an appropriate adhesive. The said adhesive could be applied directly to either the outer bag material or to the hydrocolloid flange. Alternatively, the hydrocolloid adhesive itself may be employed. The adhesive could also be provided on a separate adhesive layer which could itself be either attached by, for example, welding or adhesively to either the outer bag material or to the hydrocolloid flange.

The inner bag or liner in general is attached to the flange in a more permanent manner; there being no line or area of weakness to enable detachment of the inner bag.

The outer bag most preferably is formed of a material which acts as a barrier to flatus gases. Examples of materials from which the outer bag can be formed include polyvinyl chloride (PVC), polyvinyl dichloride (PVDC), ethylene vinyl alcohol, and related materials and combinations thereof. However, in order to prevent the undesirable build-up of flatus gases within the bag, the wall of the outer bag can be provided with a flatus filter which permits the egress of gas from the bag but which filters out malodorous and noxious gases. Such filters, which can contain activated charcoal for the absorption of malodorous and noxious gases, are well known and need not be described in detail here.

As stated hereinbefore, the outer bag is intended to be torn or peeled away from the inner bag and flange after use and, since it is not soiled by the collected waste materials, it can simply be disposed of in a waste bin along with other household waste. Thus, it is not necessary for the outer bag to be water-soluble, or even biodegradable over a short period. Consequently, the outer bag can be made as tough and as waterproof as the circumstances of use demand.

However, the inner bag is intended to be flushable and consequently is of a structure which is weakened upon immersion in a W.C. bowl, such that it becomes limp and is less buoyant thereby enabling it to be flushed away easily.

Preferably, the inner bag is formed so as to have a water-impermeable layer and, disposed externally thereof, a water-soluble layer. For example, the inner bag can be formed from a polymeric film which is water-impermeable and only marginally water-soluble on one surface thereof, and highly water-soluble on another surface thereof. With such an arrangement, upon immersion of the inner bag in water, the water-soluble layer dissolves rapidly, weakening the inner bag, such that it becomes limp thereby allowing it to be flushed more readily.

In one embodiment the inner bag can be formed of a material comprising two polymeric films laminated together, one polymeric film being water-impermeable and the other polymeric film being water-soluble. The two polymeric films can be formed of different polymers, or they can be formed of substantially the same type of polymer, but wherein one film has been treated to render it water-impermeable. Alternatively, the inner bag can be formed from two different grades of the same polymer. The two films can be of approximately the same thickness and tensile strength. Examples of polymeric materials which can be employed include poll;vinyl alcohol, alginates, starches and starch derivatives and cellulose derivatives.

The inner bag is most preferably permeable to flatus gases.

In another embodiment, the water-soluble layer can comprise a water-soluble polymer in fibrillated film, net or textile form (e.g. a non-woven form) laminated to the water-impermeable layer.

The water-soluble layer typically is formed of a material such that at least 50%, preferably 75% and more preferably 90% by weight, disperses or dissolves in water at 50° within 10 seconds.

Although the inner bag is water-impermeable, it is nevertheless most preferred that the entire inner bag should be biodegradable, and preferably complete degradation of the bag occurs within five days of immersion in mildly turbulent water.

The inner bag can advantageously be lined with a fine coating of a hydrophobic material such as silicones, PTFE, oils, waxes and lacquers, or a coating of a metallic film or deposited metal layer which serves to increase water-impermeability whilst not adding appreciably to the mechanical strength of the bag.

In a further aspect, the present invention provides a drainage bag (e.g. an ostomy bag) for receiving bodily waste, the bag being formed from a polymeric material, the inner surface of which bears a coating of a hydrophobic material, e.g. as hereinbefore defined, or a metallic coating or deposited metal layer which is substantially impermeable to water. Such drainage bags can take the form of the bags described hereinabove.

BRIEF DESCRIPTION OF THE DRAWINGS

The invention will now be illustrated, but not limited, by reference to the specific embodiment shown in the accompanying drawings, in which.

DESCRIPTION OF ILLUSTRATED EMBODIMENT

Figure 1:
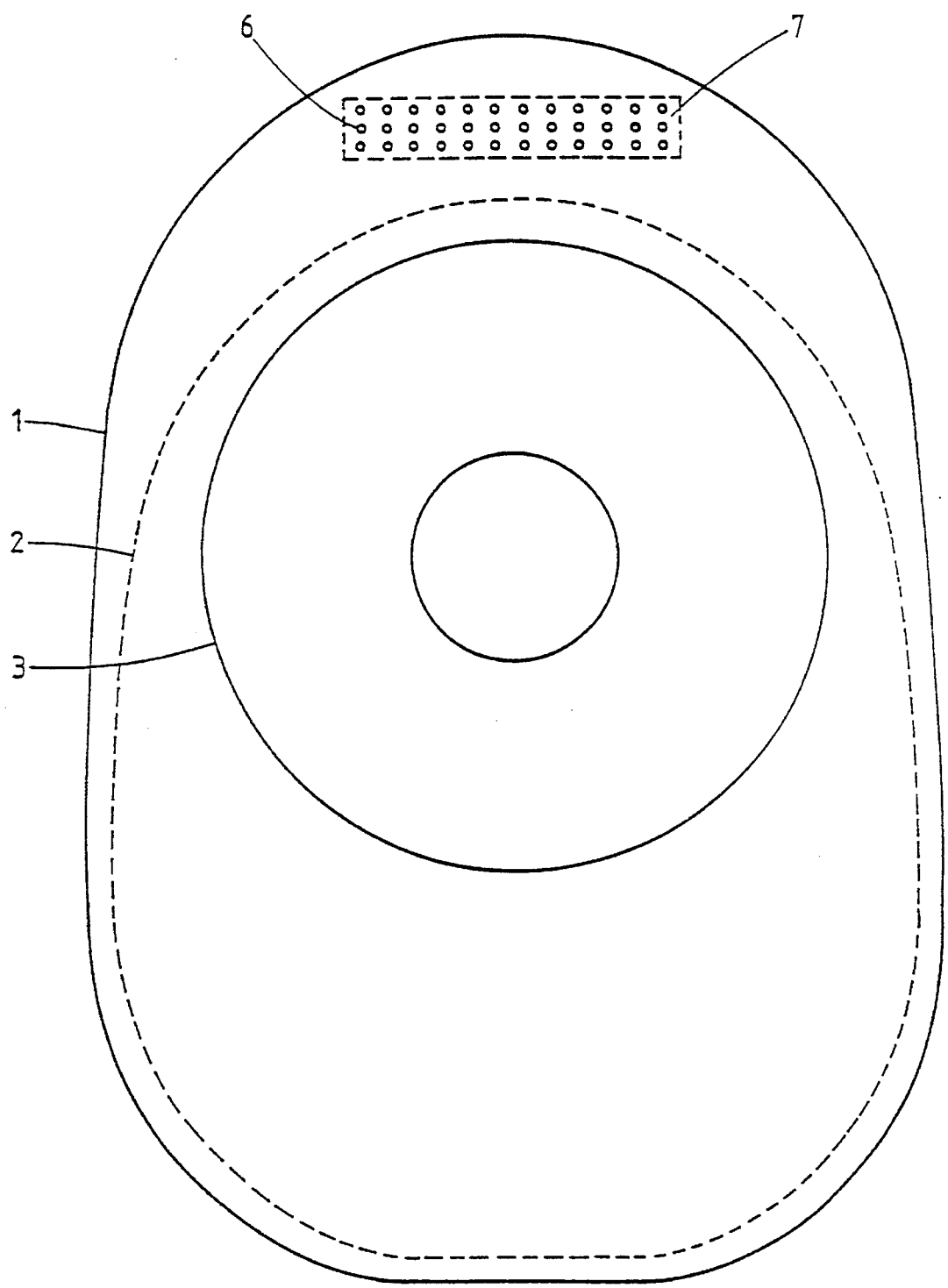
FIG. 1 is a view from one side of an ostomy bag according to one embodiment of the invention.

Referring to the drawings, it can be seen that an ostomy bag according to one embodiment of the invention comprises an outer bag 1 and an inner bag or liner 2. The outer bag 1 and liner 2 have openings at their upper ends and are both secured by thermal welding to one surface of the annular flange 3. Annular flange 3 is provided on its external surface with a layer of hydrocolloid adhesive 4 which enables the bag to be affixed to the body wall of a patient about the stomal opening: see FIGS. 5 and 6. A peelable paper layer 5 protects the hydrocolloid adhesive prior to use.

In the upper part of the outer bag 1 there is provided an elongate array of perforations 6 in the bag wall. Flatus filter 7, which is of conventional construction, but is of elongate form rather than the conventional circular form, is secured against the inner surface of the bag wall, and serves to allow flatus gases to escape from the bag, the malodorous or noxious components of the flatus gases being retained by the filter. The elongate form of the filter serves as a finger-grip which assists in the tearing away of the outer bag 1. However, the filter need not be of this shape, and the conventional round filter can be used if desired.

Outer bag 1 is formed from two sheets 1a and 1b of a tough, flexible, transparent, waterproof material such as polyvinyl chloride, polyvinyl dichloride, ethylene vinyl alcohol, related material or combinations thereof, which is substantially impermeable to gases, at least over the period of use of the bag. The two sheets 1a and 1b are welded together around their peripheries in standard fashion.

Figure 2:
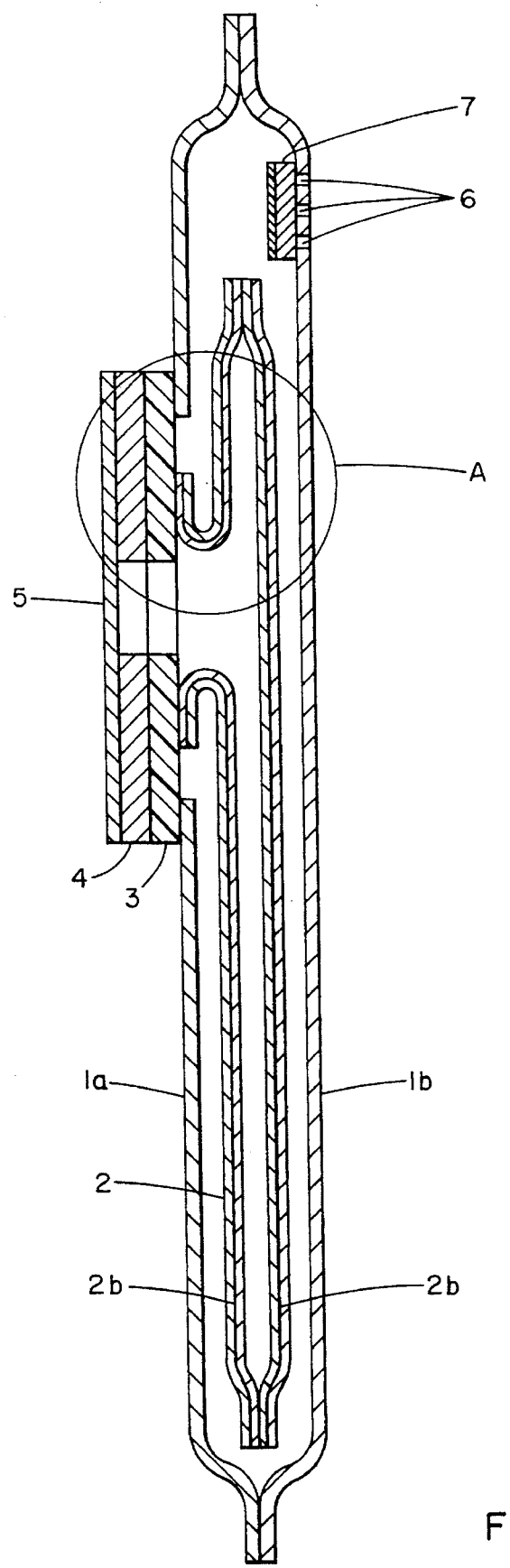
FIG. 2 is a sectional view along line I—I in Figure
Figure 2A:
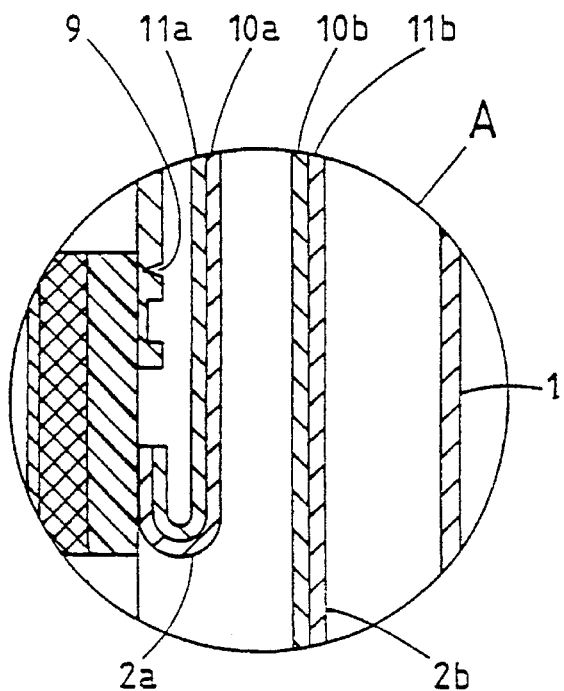
FIG. 2A is an enlarged view of the portion marked A in FIG. 2.

The manner of attachment of the outer bag 1 to the annular flange 3 is illustrated in more detail in Figure 2A. Thus, in addition to the depressions 8 left by the welding tool when the bag 1 is welded to the flange 3, there is a much deeper depression 9 formed by "over-embossing" with the welding tool and this represents an annular line of weakness.

Figure 2B:
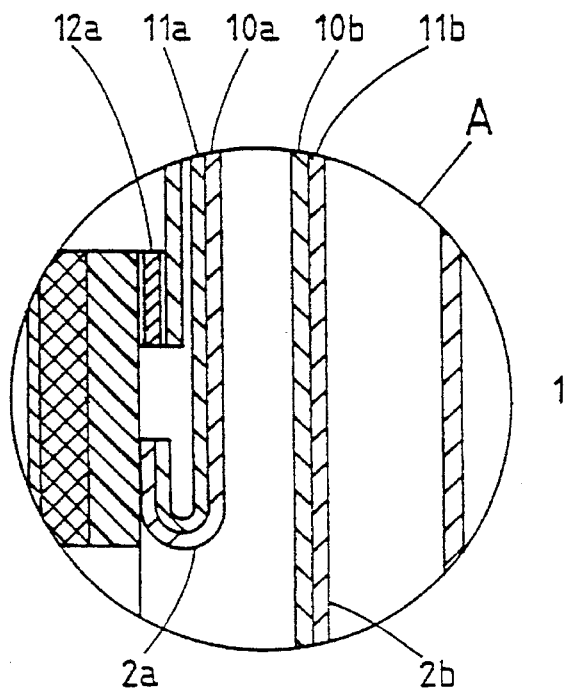
FIG. 2B is an enlarged view corresponding to the portion marked A in FIG. 2 but illustrating an alternative form of construction.

An alternative mode of attachment is shown in FIG. 2B. According to this alternative embodiment, the outer bag 1 is not welded to the flange 3 but rather is secured with peelable double-sided adhesive tape 12.

The inner bag or liner 2 is similarly formed from two sheets 2a and 2b welded together around their peripheries, but the sheets 2a and 2b are of laminar structure being formed from discrete films 10a and 11a, and 10b and 11b respectively. The films 10a and 10b in this embodiment are formed from a grade of polyvinyl alcohol which is only slowly soluble in cold water but is soluble in hot water. Examples of such a material are the "BP 26 mic", "LA-60 25 mic" and "NP 40 mic" grades of polyvinyl alcohol films manufactured by The Aicello Chemical Company Limited, Aichi, Japan, the properties of which are given in Section III of Table 1.

The films 10a and 10b function as the water-impermeable layer.

Films 11a and 11b, in this embodiment, are formed of a more soluble grade of polyvinyl alcohol, for example one of the cold water-soluble partially hydrolysed grades set out in section I of Table 1 or the cold water-soluble modified copolymer grades set out in Section II of Table 1 below.

TABLE 1

PVA FILMS :- MECHANICAL CHARACTERISTICS
20° C., 60% RHO

| | \multicolumn{7}{c}{Item} | | | | | | |
|---|---|---|---|---|---|---|---|
| | Tensile stir. (kg/mm2) | | Elongation (%) | | 10% Young's Modulus | | Impact strength at −10° C. |
| Grade | MD | TD | MD | TD | MD | TD | kg-cm (14° F.) |
| KA 40 mic. | 2.6–3.1 | 2.3–3.8 | 290–340 | 330–380 | 3.0–5.0 | 3.5–5.0 | 7.00 |
| KB 40 mic. | 2.5–3.0 | 2.0–2.5 | 300–350 | 350–400 | 3.0–5.0 | 3.0–5.0 | 9.00 |
| KC 40 mic. | 2.9–3.5 | 2.0–2.3 | 250–300 | 310–360 | 3.0–5.0 | 3.0–5.0 | 9.00 |
| KD 40 mic. | 2.8–3.3 | 2.0–2.4 | 330–380 | 330–380 | 3.0–5.0 | 3.0–5.0 | >10.00 |
| KL 40 mic. | 2.6–3.1 | 2.9–5.5 | 240–290 | 230–290 | 4.0–6.0 | 4.5–6.5 | 7.00 |
| NA 20 mic. | 2.7–3.2 | 2.4–2.9 | 160–210 | 180–230 | 7.0–9.0 | 7.0–9.0 | 3.00 |
| SA 17 mic. | 1.3–1.8 | 1.1–1.6 | 200–250 | 200–250 | 4.5–6.5 | 4.5–6.5 | 3.00 |
| PH 40 mic. | 1.3–1.8 | 1.0–1.5 | 240–290 | 280–330 | 2.0–4.0 | 2.0–4.0 | 6.00 |
| PW 40 mic. | 3.5–4.0 | 3.2–3.7 | 190–240 | 190–240 | 7.5–9.5 | 7.5–9.5 | 8.00 |
| BP 26 mic. | 2.5–3.0 | 3.3–3.8 | 270–320 | 340–390 | 6.0–8.0 | 6.0–8.0 | 5.00 |
| LA-60 25 mic. | 3.1–3.6 | 3.1–3.6 | 280–330 | 300–350 | 7.0–9.0 | 7.0–9.0 | 7.00 |
| NP 40 mic. | 3.6–4.0 | 3.3–4.0 | 250–300 | 280–320 | 6.1–7.3 | 4.5–7.6 | 8.00 |

Temperature 20° C.

Figure 3:
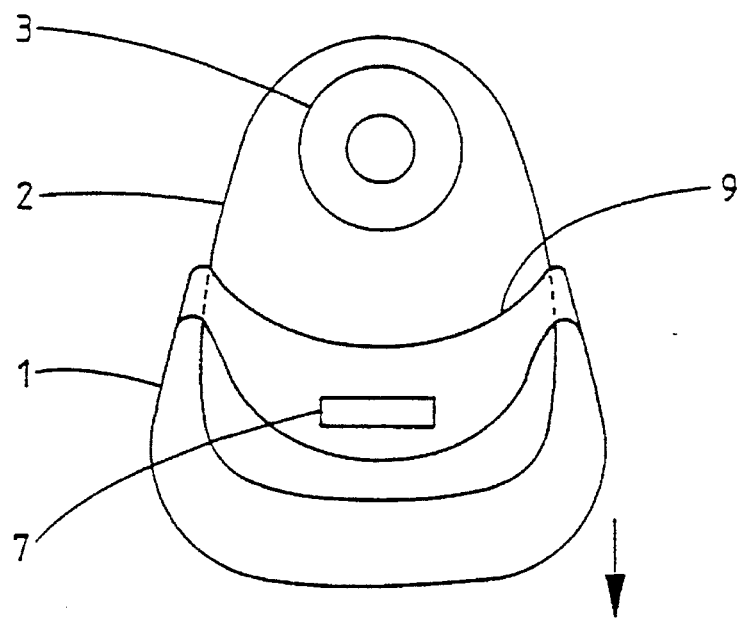
FIG. 3 is a side view showing the ostomy bag of FIGS. 1 and 2 in a partially disassembled state.
Figure 4:
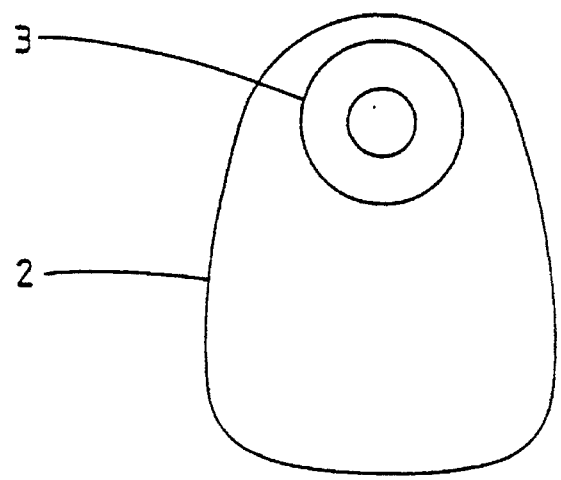
FIG. 4 is a side view showing the inner liner bag of the embodiment shown in FIGS. 1 to 3.
Figure 5:
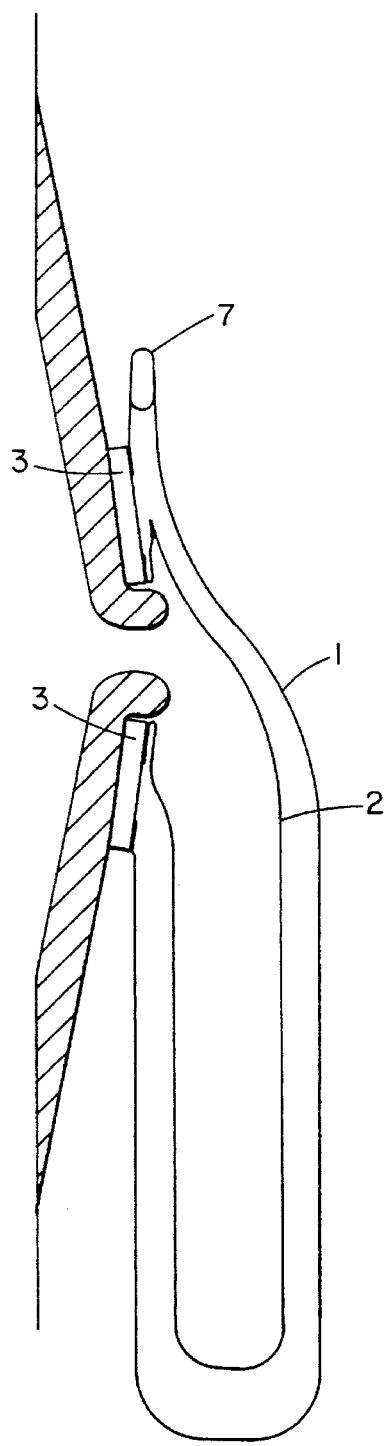
FIG. 5 is a side sectional view illustrating the mode of attachment of the ostomy bag to a patient.
Figure 6:
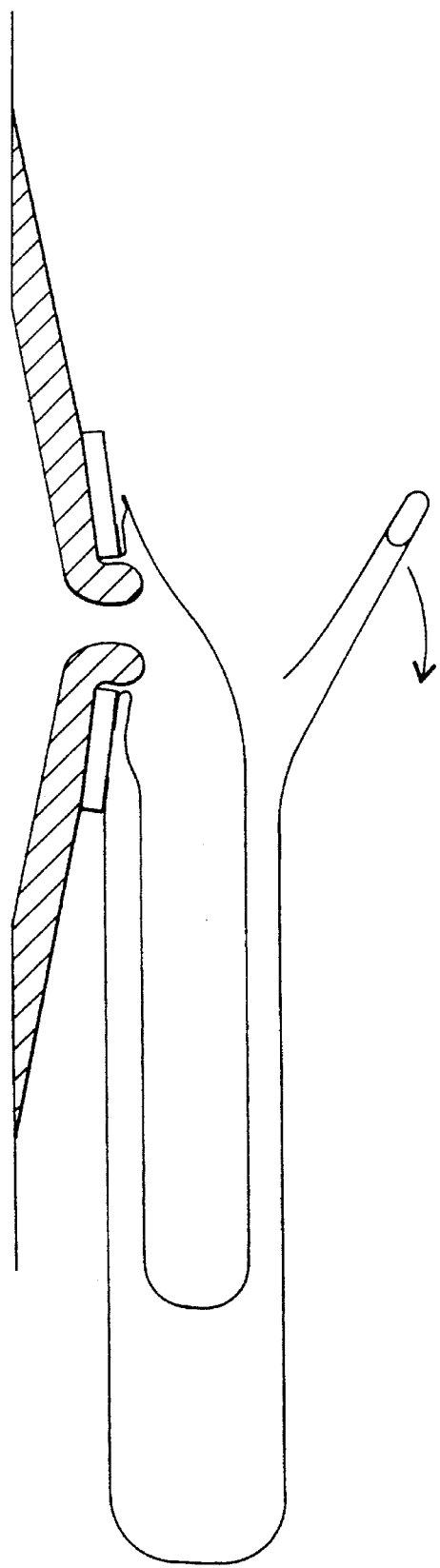
FIG. 6 is a side sectional view showing the detachment of the outer bag from the inner liner.

As can be seen from Table 1, films 10*a* , 10*b* and 11*a*, 11*b* are of approximately the same mechanical strength as defined by their tensile strengths, elongation, Young's Modulus and Impact Strengths. In use, the ostomy bag is applied to the patient as shown in FIG. 5. When the bag is full and/or it is desired to remove the contents, the outer bag 1 is detached from the flange 3 by tearing along the line of weakness 9, as shown in FIGS. 3 and 5. Alternatively, if the outer bag 1 is secured to flange 3 by means of adhesive or adhesive tape, it can simply be peeled away from the flange 3. The outer bag wall in general is uncontaminated by bodily waste and can be disposed of by placing in a domestic household waste bin. The inner bag 2 is carefully removed from the body and dropped into the bowl of a W.C. The water-soluble layers 11*a*,11*b* of the inner bag 2 rapidly dissolve causing the inner bag to become limp thereby conforming more closely to the contours of its contents and reducing its buoyancy. The inner bag 2 can then be easily flushed away.

The foregoing description is merely exemplary of one embodiment of the invention and it will readily be apparent that numerous modifications and alterations can be made without departing from the principles underlying the invention. For example, the layer 11*a*, 11*b* of the inner bag can be replaced by a layer of fibrous or non-woven textile material. In addition, or alternatively, the layer 10*a*,10*b* can be provided with a hydrophobic coating or a deposited metallic layer to provide a longer-lasting water-impermeability. Such a coating or metallic layer need only be a few molecules thick and would not impart any appreciable additional mechanical strength to the bag.

All such modifications and alterations are intended to be embraced by this application.

We claim:

1. A drainage bag for receiving bodily waste, the drainage bag comprising:

a water-impermeable outer bag formed from a material which acts as a barrier to flatus gases, the outer bag being provided with a flatus filter;

a water-impermeable inner bag enclosed within the outer bag, the inner bag being permeable to flatus gases, and being of a structure which is weakened upon immersion in a WC bowl such that it becomes limp and is less buoyant thereby enabling it to be flushed away easily;

and means defining an orifice to enable bodily waste to be received by the inner bag, and including a flange having first and second sides, on the first side of which is an adhesive for adhering the bag to a patient and on the second side of which are attached the inner and outer bags; and wherein the outer and inner bags being detachably secured together in the region of the orifice.

2. The drainage bag according to claim 1 which is an ostomy bag.

3. The drainage bag according to claim 1 wherein the inner and outer bags are detachably secured together by means of a frangible or peelable connection or linkage.

4. The drainage bag according to claim 1 wherein the outer bag is frangibly or peelably attached to the flange.

5. The drainage bag according to claim 4 wherein the outer bag is welded to the flange and is detachable therefrom by virtue of a line of weakness in the region of the weld.

6. The drainage bag according to claim 1 wherein the line of weakness in created whilst the outer bag is being welded to the flange.

7. The drainage bag according to claim 4 in which the outer bag is adhesively secured to the flange either directly or via an additional layer.

8. The drainage bag according to claim 1 wherein the inner bag is formed so as to have a water-impermeable layer and, disposed externally thereof, a water-soluble layer.

9. The drainage bag according to claim 8 wherein the inner bag is formed from a polymeric film which is water-impermeable and only marginally water-soluble on one surface thereof and highly water-soluble on another surface thereof.

10. The drainage bag according to claim 8 wherein the inner bag is formed of a material comprising two polymeric films laminated together, one polymeric film being water-impermeable, and other polymeric film being water-soluble.

11. The drainage bag according to claim 10 wherein both polymeric films are formed of substantially the same type of polymer, but wherein one film has been treated to render it water impermeable.

12. The drainage bag according to claim 11 wherein the polymeric films are of approximately the same thickness and tensile strength.

13. The drainage bag according to claim 8 wherein the water-soluble layer comprises a water-soluble polymer in fibrillated film, net or textile form laminated to the water-impermeable layer.

14. The drainage bag according to claim 1 wherein the water-soluble layer is formed of a material such that at least 50% by weight disperses or dissolves in water at 50° C. within 10 seconds.

15. The drainage bag according to claim 1 wherein the inner bag is biodegradable.

16. The drainage bag according to claim 1 wherein the inner bag is formed of a material such that substantially complete degradation of the bag occurs within 5 days of immersion in mildly turbulent water.

17. The drainage bag according to claim 1, the inner bag being formed from a polymeric material, the inner surface of which bears a coating of a hydrophobic material, or a metallic coating or deposited metal layer which is substantially impermeable to water.

18. The drainage bag according to claim 17 wherein the inner surface of the inner bag is provided with a coating of hydrophobic material selected from silicones. PTFE, oils, waxes and lacquers.

* * * * *